(12) United States Patent
Jia et al.

(10) Patent No.: US 6,210,680 B1
(45) Date of Patent: Apr. 3, 2001

(54) METHOD FOR THE PREVENTION AND TREATMENT OF CHRONIC VENOUS INSUFFICIENCY

(75) Inventors: Qi Jia, Arvada; Zhihua Qiu, Westminster; Ajith Nissanka, Boulder; Belaid Mahiou, Westminster; Thomas M. Farrow, Denver, all of CO (US)

(73) Assignee: Univera Pharmaceuticals, Inc., Broomfield, CO (US)

( * ) Notice: Subject to any disclaimer, the term of this patent is extended or adjusted under 35 U.S.C. 154(b) by 0 days.

(21) Appl. No.: 09/329,848

(22) Filed: Jun. 11, 1999

(51) Int. Cl.$^7$ ............................. A01N 65/00; A01N 35/78
(52) U.S. Cl. ........................................ 424/195.1; 514/185
(58) Field of Search ......................... 424/195.1; 514/185

(56) References Cited

U.S. PATENT DOCUMENTS

| | | |
|---|---|---|
| 4,120,964 | 10/1978 | Hartenstein et al. . |
| 4,202,980 | 5/1980 | Hartenstein et al. . |
| 4,265,912 | 5/1981 | Wang . |
| 4,309,542 | 1/1982 | Hartenstein et al. . |
| 4,315,010 | 2/1982 | Wang . |
| 4,353,912 | 10/1982 | Neumeyer . |
| 4,358,592 | 11/1982 | Goralski . |
| 4,461,895 | 7/1984 | Fritschi et al. . |
| 4,543,256 | 9/1985 | Neumeyer . |
| 4,687,773 | 8/1987 | Neumeyer . |
| 4,761,417 | 8/1988 | Maroko . |
| 4,767,626 | 8/1988 | Cheng . |
| 4,797,392 | * 1/1989 | Chernomorsky ..................... 514/185 |
| 5,137,912 | 8/1992 | Teng et al. . |
| 5,153,178 | 10/1992 | Maroko . |
| 5,156,847 | 10/1992 | Lewis et al. . |
| 5,198,230 | 3/1993 | Wen . |
| 5,258,384 | 11/1993 | Cannon et al. . |
| 5,395,615 | 3/1995 | Godowski et al. . |
| 5,466,452 | 11/1995 | Whittle . |
| 5,474,782 | 12/1995 | Winter et al. . |
| 5,562,906 | * 10/1996 | Terry et al. ....................... 424/195.1 |
| 5,594,033 | 1/1997 | Su et al. . |

FOREIGN PATENT DOCUMENTS

| | | |
|---|---|---|
| 05201833 | 8/1993 | (JP) . |
| 06211678 | 8/1994 | (JP) . |
| 07324039 | 12/1995 | (JP) . |

OTHER PUBLICATIONS

Martini, Fredric : Fundamentals of Anatomy and Physiology 2nd Ed. p. 809, 1992.*
Berkow, Robert M.D. et al. The Merck Manual 16th Ed. pp. 590–592, 855–856, 1992.*
Gray et al. Lloydia vol. 38 pp. 268–270, 1975.*
Nishiki et al. (1988) Folia Pharmacology Japan 92:215–225.
Nishiki et al. (1988) Folia Pharmacol. Japan 92:227–240.

* cited by examiner

Primary Examiner—Jon P. Weber
Assistant Examiner—Patricia Patten
(74) Attorney, Agent, or Firm—Swanson & Bratschun, L.L.C.

(57) ABSTRACT

The present invention provides a method for the prevention and treatment of chronic venous insufficiency. Specifically, the present invention provides a method for the prevention and treatment of varicose veins, particularly hemorrhoids by application of an effective amount of an isoquinoline alkaloid. Included in this invention is an improved method for isolating and purifying alkaloids, particularly isoquinoline alkaloids from plants.

11 Claims, 4 Drawing Sheets

ASARININ

LIRIODENINE

CHELERYTHRINE

MAGNOFLORINE

LAURIFOLINE

METHOD FOR THE PREVENTION AND TREATMENT OF CHRONIC VENOUS INSUFFICIENCY

FIELD OF INVENTION

The present invention relates generally to a method for the prevention and treatment of chronic venous insufficiency. Specifically, the present invention relates generally to a method for the prevention and treatment of varicose veins, particularly hemorrhoids by administration of an isoquinoline alkaloid. Included in this invention is an improved method for isolating and purifying alkaloids, particularly isoquinoline alkaloids from plant sources.

BACKGROUND OF THE INVENTION

Varicose veins are swollen and knotted veins that are both unsightly and uncomfortable. Up to 20% of the adult population have varicose veins and experience discomfort as a result. They can cause swelling of the legs and feet and the skin to itch. Factors such as prolonged standing or sitting, obesity and pregnancy play a large part in the development of varicosity. Varicose veins can occur in almost any part of the body, however they most often occur in the calf or on the inside of the leg between the groin and the ankle.

Hemorrhoids are a varicose dilation of the veins around the anus. Hemorrhoids are similar to varicose veins in the legs, in that the supporting walls of the veins weaken. According to the National Institutes of Health, about half of the United States population over age 50 suffer from hemorrhoids. While most hemorrhoids are not serious, they can have a major effect on one's quality of life. Prevention and treatment of hemorrhoids can include dietary changes, stool softeners, sitz baths and application of conventional topical anti-inflammatory ointments, such as Hemorid, Hemcure, Hemorr-X, Delicare, Preparation H and Ultroid. In more extreme cases, destroying the hemorrhoid by freezing or heating, ligation of the hemorrhoid or even laser surgery may be warranted. There are also a variety of traditional remedies available in India, China and other countries.

Alkaloids are basic nitrogenous organic compounds of plant origin. Isoquinoline alkaloids are a class of alkaloids derived from isoquinoline which has the following structure:

Aporphine alkaloids, are a class of isoquinoline alkaloids, which have the following general structure:

wherein $R_1$, and $R_2$ are independently selected from the group consisting of H, alkyl, substituted alkyl, cycloalkyl, substituted cycloalkyl, alkenyl or substituted alkenyl, methylene; $R_3$, $R_4$, $R_5$, $R_6$, $R_7$ and $R_8$ are independently selected from the group consisting of H, hydroxy, thiol, methoxy, methyl sulfide, methylenedioxy, alkoxy, alkyl sulfide or pharmaceutically acceptable acid addition salts, selected from the group consisting of chloride, iodide, fluoride, sulfate, phosphate, acetate or carbonate. Apolphine alkaloids have been isolated from the genera of more than twenty plant families, including but not limited to, Araceae, Aristolochiaceae, Berberidaceae, Euphorbiaceae, Helleboraceae, Lauraceae, Magnoliaceae, Menispermaceae, Papaveraceae, Ranunculaceae, Rhamnaceae and Rutaceae. Within these plant families aporphine alkaloids have been isolated from species in numerous genera, including but not limited to, Aconitum, Aristolochia, Berberis, Chelidonium, Clemnatis, Cocculus, Coplis, Dioscoreophyllum, Epimedium, Fumaria, Glaucium, Magnolia, Mahonia, Manodora, Nandina, Pachygone, Phellodendron, Ranunculus, Sinomenium, Thalictrum, Tinospora and Zanthoxylunm. Aporphine alkaloids can be isolated from the whole plant, stems, stem bark, twigs, tubers, flowers, fruits, roots, root barks, young shoots, seeds, rhizomes and aerial parts. To date, more than 500 aporphine alkaloids have been synthesized and/or isolated from more than 90 genera of plants.

Aporphine alkaloids have been reported as having diverse biological activity. Compounds within this class of alkaloids have been patented for the treatment of duodenal ulcers and epileptic seizures (U.S. Pat. Nos. 4,543,256 and 4,543,256), cardiac arrhythmia (U.S. Pat. No. 5,594,033), hypertension (U.S. Pat. No. 4,120,964) and colds and allergies (U.S. Pat. No. 4,461,895). Compounds within this class of alkaloids have also been reported to enhance dopaminergic activity by inactivating a dopamine receptor (U.S. Pat. Nos. 4,353,912 and 4,687,773), improve circulatory performance (U.S. Pat. Nos. 4,761,417 and 5,153,178) and improve wound-healing (U.S. Pat. Nos. 5,156,847 and 5,474,782). Finally, compounds within this class of alkaloids have been reported as an antidote to counteract the effects of cocaine, as appetite suppressants (U.S. Pat. No. 5,258,384), as having analgesic and antitussive effects (U.S. Pat. Nos. 4,358,592, 4,265,912 and 4,315,010) and antipsychotic or sedative effects (U.S. Pat. No. 4,687,773). A number of these compounds have been prepared by synthetic processes (see, e.g., U.S. Pat. Nos. 4,309,542 and 4,202,980).

Magnoflorine (see FIG. 1) is a typical aporphine alkaloid, which is widely distributed in a number of plant families, including but not limited to, Aristolochiaceae, Berberidaceae, Helleboraceae, Magnoliaceae, Menispermaceae, Papaveraceae, Ranunculaceae, Rhamnaceae and Rutaceae. Magnoflorine has been shown to decrease arterial blood pressure by activation of the nicotinic receptors in the parasympathetic ganglia and the release of the vasodilator ACh in a dose-dependent manner, without affecting the heart rate and the respiration; induce dose-dependent hypothermia resulting from peripheral vasodilation: induce contractions of isolated rat uterus; and suppress the induction phase, but not the effector phase of the cellular immune response. This compound has also been reported as having antimicrobial activity, significant cytotoxicity, and to inhibit lipoxygenase. To date there have been no reports of the use of this compound for the prevention and treatment of venous insufficiency.

Benzophenanthridine alkaloids, are another class of isoquinoline alkaloids having the following structure:

wherein $R_1$, $R_2$, $R_3$ and $R_4$ are independently selected from the group consisting of H, hydroxy, alkoxy, methoxy, methylenedioxy, thiol, methyl sulfide and alkyl sulfide; and $R_5$ is selected from the group consisting of H, alkyl, substituted alkyl, cycloalkyl, substituted cycloalkyl, alkenyl and substituted alkenyl. Benzophenanthridine alkaloids have been isolated from the genera of numerous plant families, including but not limited to, Rutaceae, Fumariaceae, Papaveraceae, Caprifoliaccae, Mrliaceae. Within these plant families these alkaloids can be isolated from numerous genera including, but not limited to, Zanthoxylum, Xanthoxylium, Toddalia, Chelidonium, Papaver, Hypecoum, Hylonlecon, Prantl, Argemone, Eschscholtxia, Sanguinaria, Corydalis, Dicentra, Fumaria, Fagara, Symphoricarpos, Bocconia, Xylocarpus, and Mocleaya. Benzophenanthridine alkaloids have also been reported as having diverse biological activity. Chelerythrine (see FIG. 1) has been reported for use as an anti-hypertensive and as an inhibitor of platelet aggregration. (U.S. Pat. No. 5,137,912, issued 1992).

Zanthoxylum (also referred to in the literature as Xanthoxylum), a member of the Yellow Wood family (Rutaceae), is a widely distributed genus of plants which has more than thirty species. Two species of Zanthoxylum are indigenous to the mainland of the United States: *Z. americanum* Mill. (Northern prickly Ash) and *Z. clava-herculis L.* (Southern prickly Ash), these two species are referred to herein collectively as Prickly Ash. Prickly Ash, commonly known as the toothache tree, is a shrub or small tree, 5–10 feet in height, which has had a long history as a botanical remedy. It is a traditional native North American remedy for toothaches. This plant has also been used as an internal treatment for ulcers, skin sores, diarrhea, indigestion and circulatory problems; and as an external remedy for chronic joint pain and rheumatism. The plant parts used are the bark and fruit. The stem bark of Zanthoxylum is a rich source of alkaloids and lignans. Chemical investigations on the bark of Prickly Ash have led to the isolation of a number of lignans and alkaloids, including both benzophenanthridine and aporphine alkaloids. Northern Prickly Ash is native to southern Canada and northern, central and western parts of the United States. The bark is harvested in spring and fall and the berries are collected in summer. Dry prickly ash bark powders are available in the botanical raw materials market. Southern Prickly Ash is native to central and southern United States.

There have been numerous reports of Prickly Ash and its active ingredients having diverse biological activity, including high protein kinase C inhibition activity (Chelerythrine), anti-hypertensive activity (Asarinin), antiplatelet activity (total alkaloids and coumarins), anti-malarial activity (crude extract), neuromuscular effects (crude extract), anti-sickling activity, (benzoic acid derivatives), cytotoxic activity (alkaloids), and elevated cytochrome P450 (essential oil).

Terry et al. have disclosed a method of treating vascular disorders by administration of Xanthoxylum (Zanthoxylum). (Terry et al. U.S. Pat. No. 5,562,906, issued Oct. 8, 1996). Terry et al. did not disclose any specific compounds from the Zanthoxylum that could be used for this purpose. Other reported uses of extracts from the Zanthoxylum genus include use in herbal compositions (Japanese Patent No. 07324039JP, 1995); use in herbal powders for the treatment of addictive diseases (U.S. Pat. No. 5,198,230, 1993); use as a remedy for anemia and arthritis (U.S. Pat. No. 4,767,626, 1988); use in a cream to enhance male sexual function (Japan Patent No. 06211678JP, 1994); and use as a hair tonic (Japan Patent No.05201833JP, 1993).

Current products containing Prickly Ash bark as an ingredient include Multi nutrition Fruit Drink (minor ingredient); Pro-Essence(detoxic) herbal formula—aqueous extract (major ingredient); Circulatory tonic—aqueous extract (major ingredient); and Self defense (bark powder).

SUMMARY OF THE INVENTION

The present invention includes a method for the prevention and treatment of chronic venous insufficiency. Specifically, the present invention includes a method for the prevention and treatment of varicose veins, particularly hemorrhoids by administration to a patient in need thereof an effective amount of an isoquinoline alkaloid. In one embodiment of the present invention the isoquinoline alkaloid is selected from the group consisting of aporphine alkaloids and/or benzophenanthridine alkaloids. In a preferred embodiment the isoquinoline alkaloid is selected from the group consisting of Magnoflorine, Laurifoline and Chelerythrine. The isoquinoline alkaloid may be obtained by organic synthesis or it may be isolated from a plant containing said alkaloid.

This invention also includes an improved method for isolating and purifying isoquinoline alkaloids from plants containing these compounds. The improved method of the present invention comprises: extraction of the ground biomass of a plant containing a isoquinoline alkaloid; neutralization and concentration of the neutralized extract; and purification of said extract by chromatography. The present invention provides a commercially viable process for the isolation and purification of isoquinoline alkaloids having desirable physiological activity.

The advantages of using isoquinoline alkaloids, particularly Magnoflorine, Laurifoline and Chelerythrine, for the prevention and treatment of varicose veins, particularly hemorrhoids is that they are a natural alternative to conventional ointments, can be administered in convenient oral dosage with a short course of treatment, and they exhibit a remarkable curative effect against hemorrhoids. Additionally, these compounds are safe.

It is to be understood that both the foregoing general description and the following detailed description are exemplary and explanatory only and are not restrictive of the invention as claimed.

DETAILED DESCRIPTION OF THE INVENTION

The present invention includes a method for the prevention and treatment of chronic venous insufficiency. Specifically, the present invention includes a method for the prevention and treatment of varicose veins, particularly hemorrhoids by administration to a patient in need thereof an effective amount of an isoquinoline alkaloid.

In one embodiment the isoquinoline alkaloid is an aporphine alkaloid having the following general structure:

wherein $R_1$ and $R_2$ are independently selected from the group consisting of H, alkyl, substituted alkyl, cycloalkyl, substituted cycloalkyl, alkenyl or substituted alkenyl, methylene; $R_3$, $R_4$, $R_5$, $R_6$, $R_7$ and $R_8$ are independently selected from the group consisting of H, hydroxy, thiol, methoxy, methyl sulfide, methylenedioxy, alkoxy, alkyl sulfide or pharmaceutically acceptable acid addition salts, selected from the group consisting of chloride, iodide, fluoride, sulfate, phosphate, acetate or carbonate. In a preferred embodiment the aporphine alkaloid is selected from Magnoflorine, wherein $R_1$, and $R_2$=$CH_3$; $R_3$ and $R_8$=H; $R_4$ and $R_7$=$OCH_3$ and $R_5$ and $R_6$=OH or Laurifoline, wherein $R_1$ and $R_2$=$CH_3$; $R_3$ and $R_6$=OH; $R_4$ and $R_7$=$OCH_3$ and $R_5$ and $R_8$=H. (see FIG. 1).

The aporphine alkaloids of this invention may be obtained by synthetic methods or may be isolated from a plant source. The aporphine alkaloids of this invention can be isolated from the genera of numerous plant families, including but not limited to, Araceae, Aristolochiaceae, Berberidaceae, Euphorbiaceae, Helleboraceae, Lauraceae, Magnoliaceae, Menispermaceae, Papaveraceae, Ranunculaceae, Rhamnaceae and Rutaceae. Within these plant families these alkaloids can be isolated from Zanthoxylum, Tinospora, Mahonia, Phellodendron, Aristolochia, Magnolia, Thalictrum, Coplis, Magnolia, Epimedium, Ranunculus, Sinomenium, Nandina, Manodora, Berberis, Furnaria, Chelidonium, Pachygone, Dioscoreophyllum, Glauciurn, Clematis, Aconitum and Cocculus. In a preferred embodiment the plant is selected from the Zanthoxylum genus of plants, a member of the Rutaceae family. In the most preferred embodiment the plant is selected from two species of Zanthoxylum genus: *Z. americanum* Mill. (Northern prickly Ash) and *Z. clava-herculis* L. (Southern prickly Ash).

In a second embodiment the isoquinoline alkaloid is a benzophenanthridine alkaloid having the following structure:

wherein $R_1$, $R_2$, $R_3$ and $R_4$ are independently selected from the group consisting of H, hydroxy, alkoxy, methoxy, methylenedioxy, thiol, methyl sulfide and alkyl sulfide; and $R_5$ is selected from the group consisting of H, alkyl, substituted alkyl, cycloalkyl, substituted cycloalkyl, alkenyl and substituted alkenyl. In a preferred embodiment the benzophenanthridine alkaloid is Chelerythrine, wherein $R_1$ and $R_2$=$OCH_3$; $R_3$ and $R_4$ together=$CH_2$; $R_5$=$CH_3$.

The benzophenanthridine alkaloids of this invention may be obtained by synthetic methods or may be isolated from a plant source. The benzophenanthridine alkaloids of this invention can be isolated from the genera of numerous plant families, including but not limited to Rutaceae, Fumariaceae, Papaveraceae, Caprifoliaceae, Mrliaceae. Within these plant families these alkaloids can be isolated from Zanthoxylum, Xanthoxylium, Toddalia, Chelidonium, Papaver, Hypecoum, Hylomecon, Prantl, Argemone, Eschscholtxia, Sanguinaria, Corydalis, Dicentra, Fumaria, Fagara, Symphoricarpos, Bocconia, Xylocarpus, and Mocleaya. In a preferred embodiment the plant is selected from the Zanthoxylum genus of plants, a member of the Rutaceae family. In the most preferred embodiment the plant is selected from two species of Zanthoxylum: *Z. americauni* Mill. (Northern prickly Ash) and *Z. clava-herculis* L. (Southern prickly Ash).

The isoquinoline alkaloids of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof an effective amount of the isoquinoline alkaloid. Doses of the isoquinoline alkaloids and pharmaceutical compositions containing same are an efficacious, nontoxic quantity generally selected from the range of 0.01 to 50 mg/kg of body weight. Persons skilled in the art using routine clinical testing are able to determine optimum doses for the particular ailment being treated.

The preparation of products for administration in pharmaceutical preparations may be performed by a variety of methods well known to those skilled in the art. The isoquinoline alkaloid may be formulated in an herb powder, a crude herb extract, as a mixture containing enriched isoquinoline alkaloids from the plant source or as the substantially purified compound, isolated from a plant source or prepared by synthetic methods.

This invention also includes an improved method for isolating and purifying isoquinoline alkaloids from plants. This improved method comprises: extraction of the ground biomass of a plant containing a isoquinoline alkaloid; neutralization and concentration of the neutralized extract; and purification of said extract by chromatography. As provided above, these alkaloids, particularly aporphine alkaloids have been isolated from the genera of more than twenty plant families. The method of this invention can be extended to the isolation of these compounds from any plant source containing these compounds. In one embodiment the plant used is selected from the family of plants including, but not limited to, Araceae, Aristolochiaceae, Berberidaceae, Caprifoliaceae, Euphorbiaceae, Fumariaceae, Helleboraceae, Lauraceae, Magnoliaceae, Menispermaceae, Mrliaceae, Papaveraceae, Ranunculaceae, Rhamnaceae and Rutaceae. Within these plant families the plant used to isolate aporphine alkaloids is selected from a number of genera including, but not limited to, Zanthoxylum, Tinospora, Mahonia, Phellodendron, Aristolochia, Magnolia, Thalictrum, Coptis, Magnolia, Epimedium, Ranunculus, Sinomenium, Nandina, Manodora, Berberis, Fumaria, Chelidonium, Pachygone, Dioscoreophyllum, Glaucium, Clematis, Aconitum and Cocculus. For the isolation of benzophenanthridine alkaloids the plant is selected from a number of genera including, but not limited to Zanthoxylum, Xanthoxylium, Toddalia, Chelidonium, Papaver, Hypecoum, Hylomecon, Prantl, Argemone, Eschscholtxia, Sanguinaria, Corydalis, Dicentra, Fumaria, Fagara, Symphoricarpos, Bocconia, Xylocarpus, and Mocleaya. In a preferred embodiment the plant is selected from the Zanthoxylum genus of plants, a member of the Rutaceae family. In the most preferred embodiment the plant is selected from two species of Zanthoxylum genus: *Z. americanum* Mill. (Northern prickly Ash) and *Z. clava-herculis* L. (Southern prickly Ash).

Isoquinoline alkaloids can be isolated from various parts of the plant including, but not limited to, the whole plant, stems, stem bark, twigs, tubers, flowers, fruit, roots, root barks, young shoots, seeds, rhizomes and aerial parts. In a preferred embodiment the alkaloids are isolated from the stem and stem bark or the whole plant.

The solvent used for extraction of the ground biomass of the plant includes, but is not limited to water, acidified water, an acidified water miscible hydroxylated organic solvent including, but not limited to, methanol or ethanol and an acidified mixture of alcohol or other water miscible hydroxylated organic solvent and water. In one embodiment the acidic extract is neutralized to pH of 4.5–5.5 with aqueous base. The neutralized extract is then concentrated and dried to yield a powder. The alkaloids can then be purified by various chromatographic methods including, but not limited to, ion exchange chromatography, absorption chromatography, reverse phase chromatography, size exclusive chromatography, ultra-filtration or a combination of two or more of these chromatographic methods.

Example 1 describes the isolation and identification of the chemical components of prickly ash bark. Using the method of Example 1, five alkaloids were isolated and identified from the bark of Southern Prickly Ash: Asarinin, a lignan, Chelerythrine, Liriodenine, Magnoflorine and Laurifoline (see FIG. 1).

Example 2 describes the determination of the alkaloid content in different species of Prickly Ash using different methods of extraction. The results of this example are set forth in Table 1. These studies demonstrate that isoquinoline alkaloids can be extracted from plants with deionized (DI) water, acidic aqueous solutions or high polarity solvents, such as ethanol, methanol, butanol with or without water. Acidic aqueous solutions are the best solvents, as they generate high extractable solids and reasonable amounts of isoquinoline alkaloids. The preferred solvent was determined to be 1% HCl in MeOH.

Example 3 describes a commercial process for the isolation of isoquinoline alkaloids from Prickly Ash bark. The preferred commercial extraction process is using a column extractor, percolating the ground biomass with 0.3% $H_2SO_4$ at 60° C. The crude extract can be concentrated using a solvent evaporator, ultra-filtration or column chromatography to reach the optimum concentration of isoquinoline alkaloids.

Example 4 describes the separation of isoquinoline alkaloids from prickly ash aqueous extract using ion exchange chromatography.

Figure 2:
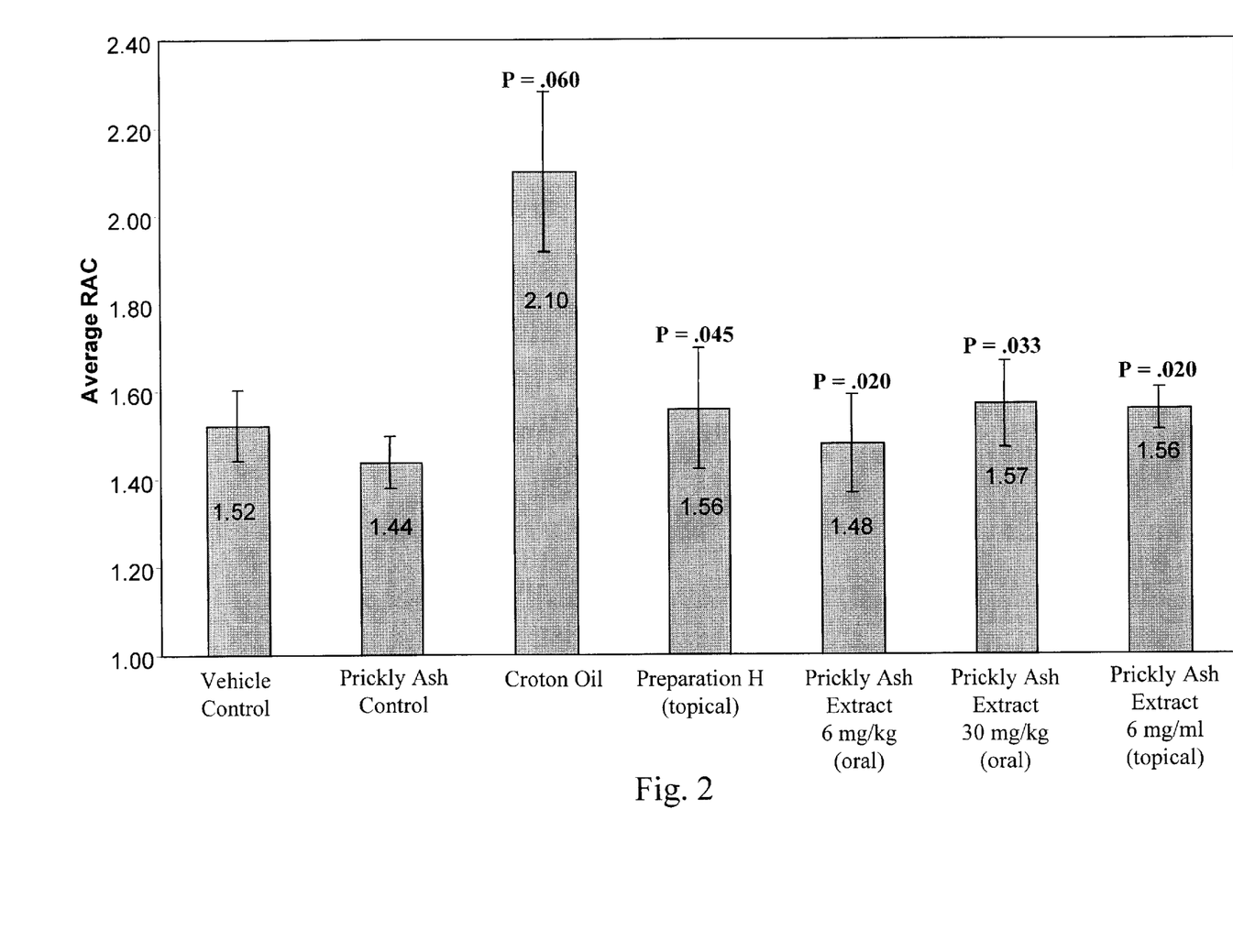
FIG. 2 illustrates graphically the results of the hemorrhoid in vivo assay using Prickly Ash extract, as described in Example 5.

Example 5 illustrates the reduction of the swelling, induced by croton oil, of the recto-anus in rats by prickly ash extract. The results are depicted in FIG. 2, which shows that the prickly ash extract, administered orally or topically, completely inhibited the swelling of the recto-anus induced by croton oil at both concentrations studied.

Figure 3:
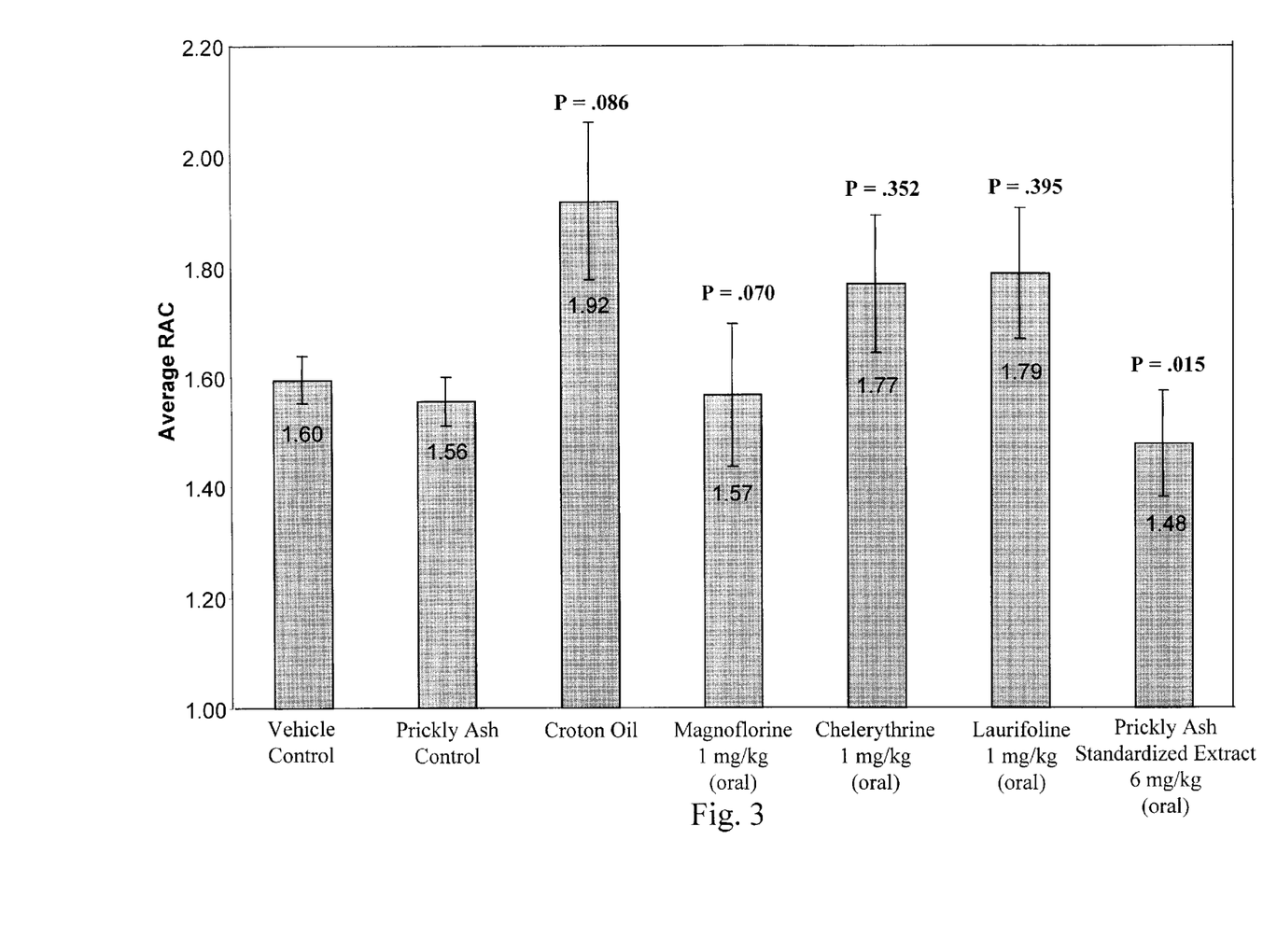
FIG. 3 illustrates graphically the results of the hemorrhoid in vivo assay using three of the isoquinoline alkaloids isolated from Prickly Ash, as described in Example 6.

Example 6 illustrates the reduction of the swelling, induced by croton oil, of the recto-anus in rats by individual isoquinoline alkaloids isolated from Prickly Ash. The results are depicted in FIG. 3, which shows that Magnoflorine completely inhibited the swelling of the recto-anus induced by croton oil. Under the same conditions, Laurifoline and Chelerythrine partially reduced the swelling.

Figure 4:
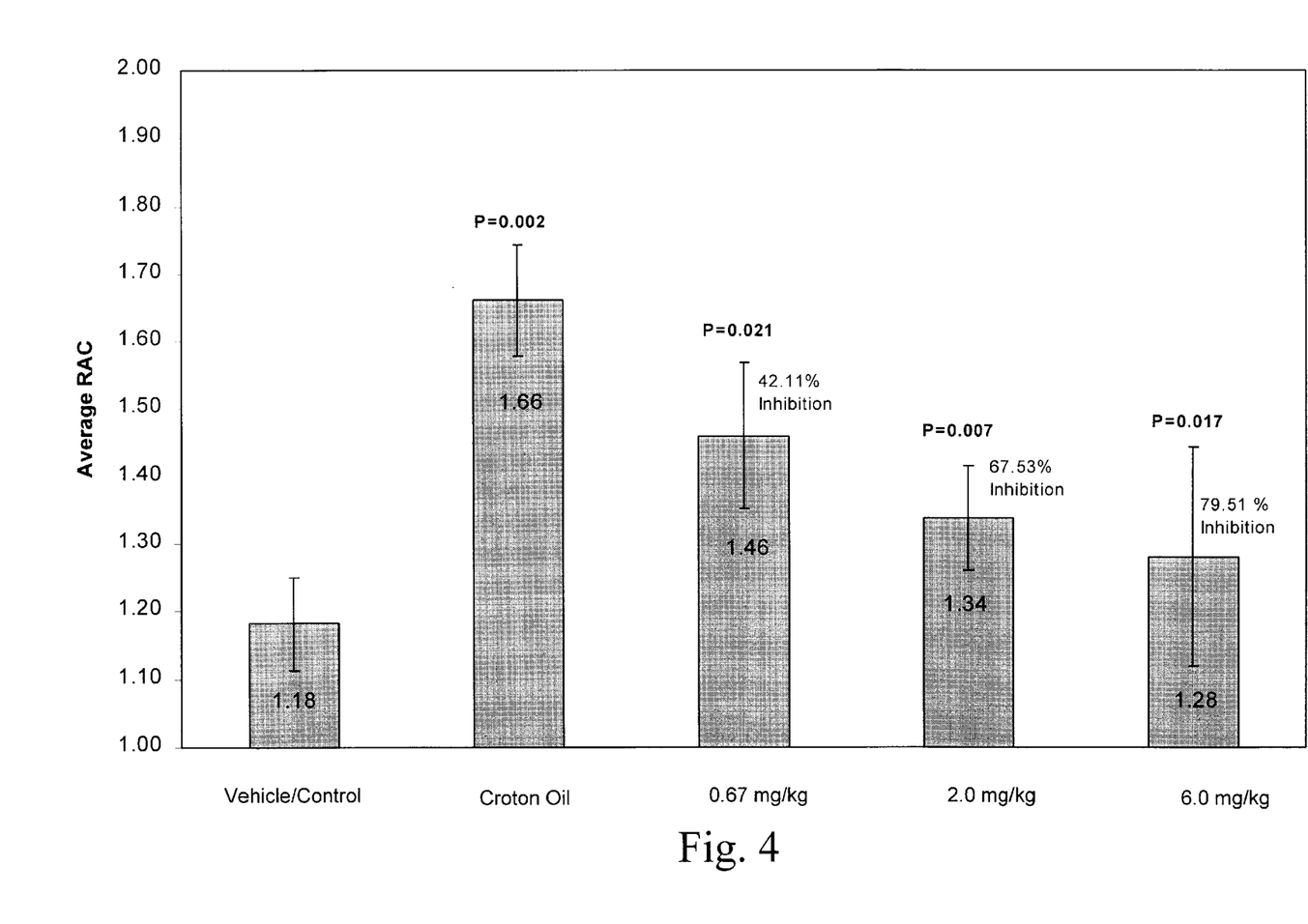
FIG. 4 illustrates graphically the dose dependent reduction of the swelling of the recto-anus induced by croton oil by Prickly Ash Extract as described in Example 7.

Example 7 illustrates the dose dependent reduction of the swelling, induced by croton oil, of the recto-anus in rats by Prickly Ash Extract. As depicted in FIG. 4, the Prickly Ash extract, administered orally, reduced the swelling of the recto-anus by 79.5%, 67.5% and 42.1%, at dosage levels of 6.0 mg/kg, 2.0 mg/kg, and 0.67 mg/kg, respectively.

The following examples are provided for illustrative purposes only and are not intended to limit the scope of the invention.

EXAMPLES

Example 1

Isolation and Identification of the Chemical Components of Prickly Ash Bark

Figure 1:
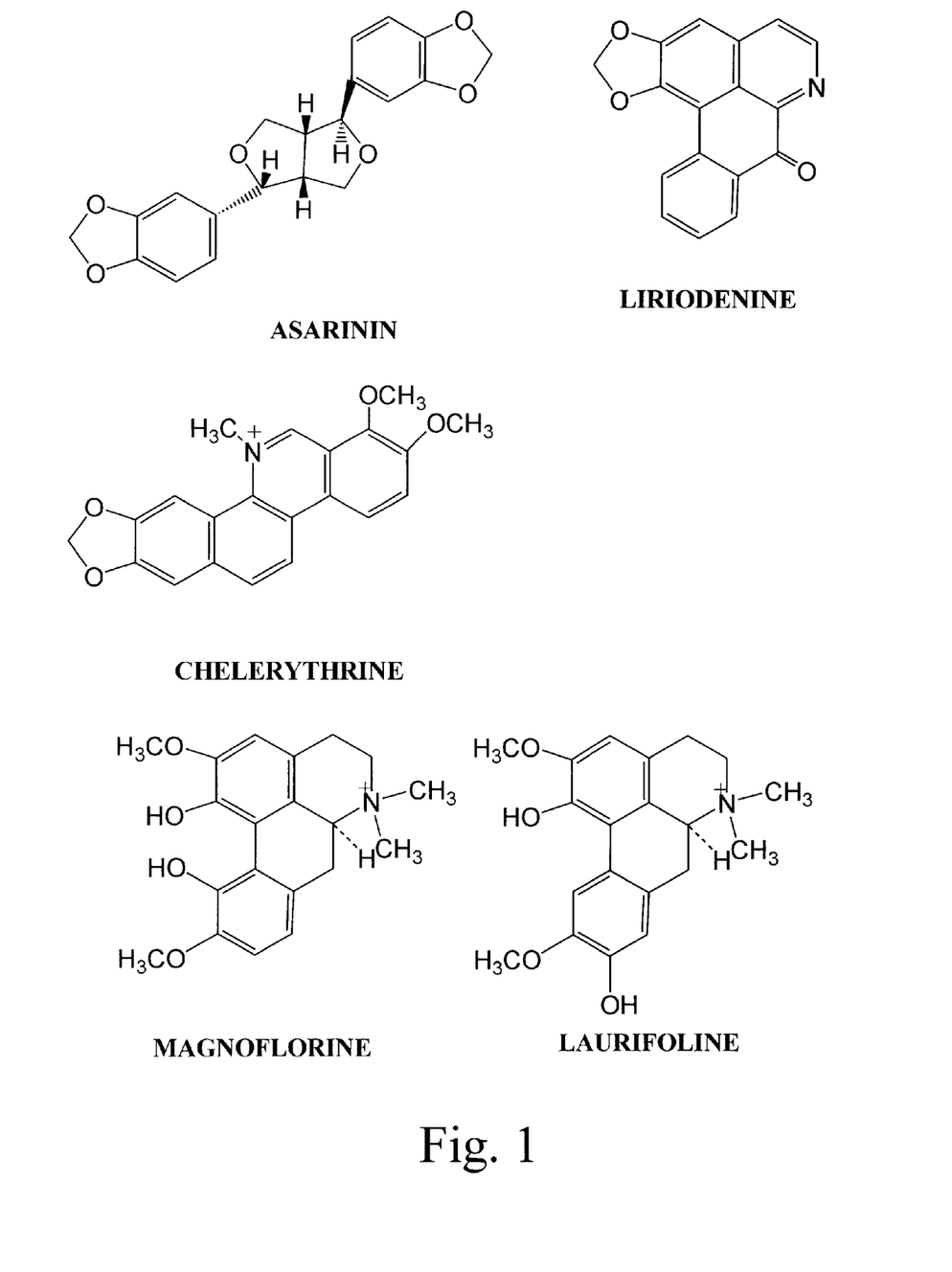
FIG. 1 depicts the chemical compounds isolated and identified from Prickly Ash bark as described in Examples 2 and 3.

Prickly Ash (*Zanthoxylum clava-hericulis*) bark, dried powdered stem bark (800 g), was exhaustively extracted using hexane followed by a mixture of methanol and dichloromethane (1:1). The hexane extract was concentrated to give a brownish oil (105 g) and the dichloromethane/methanol extract was concentrated to give a brown solid (102 g). The concentrated hexane extract (20 g) was purified by column chromatography (38 cm×5.0 cm column, silica gel), eluting with a step-wise gradient of ethyl acetate in hexane (0%–100%). A solid (1.57 g) was obtained from the fraction eluted with 30% EtOAc/hexane, which was further purified by column chromatography (38 cm×5.0 cm column, silica gel), eluting with 30% EtOAc/hexane to yield a white solid (1.0 g). The white solid (1 g) was recrystallized by dissolving it into a minimum amount of dichloromethane and by precipitating with hexane to give needle-like crystals (0.17 g). The compound isolated was identified by spectral analysis as Asarinin, a lignan (FIG. 1). UV $\lambda_{max}$ (MeOH)

nm: 207, 237, 286, 320; $^1$H NMR (CDCl$_3$) δ: 2.82 (q, 1H), 3.28 (m, 2H), 3.82 (m, 2H), 4.07 (d, 1H), 4.37 (d, 1H), 4.81 (d, 1H), 5.93 (s, 2H), 5.93 (s, 2H), 6.78 (m, 5H), 6.85 (s, 1H).

TLC analysis (2% MeOH in dichloromethane with 1% ammonium hydroxide) of the dichloromethane extract revealed the presence of two major alkaloids. The dichloromethane extract (3.2 g) was chromatographed on a medium pressure liquid chromatography column (MPLC), eluting with 6% methanol in dichloromethane. Five fractions were collected. The first fraction (0.54 g) was further purified by silica gel preparative thin layer chromatography (TLC) using 2% methanol in chloroform, to yield a greenish yellow solid (6 mg). This compound was identified as Chelerytlirine (see FIG. 1) by comparison of its TLC and spectral data with a standard solution of Chelerythrine. Chelerythrine: UV $\lambda_{max}$ (MeOH) nm : 236,282,319; IR γ (KBr): 2916,2849, 1737, 1598, 1494, 1365, 1283, 1253, 930, 876, 821.

The third fraction (3.22 g) was purified by column chromatography (38 cm×5.0 cm column, silica gel), eluting with 3% methanol in chloroform to yield 72 mg of a greenish yellow solid, which was identified as Liriodenine (see FIG. 1). UV $\lambda_{max}$ (MeOH) nm: 201.6, 222.2, 271.6, 300.60 (sh), 328.1, 385.6; $^1$H NMR (CDCl$_3$) δ: 6.28 (s, 2H), 7.05 (s, 1H), 7.47 (t, 1H), 7.64 (m, 2H), 8.41 (d, 1H), 8.48 (d, 1H), 8.70 (d, 1H).

A freeze dried sample of Prickly Ash, aqueous extract (Z. clava-herculis, 20 g) was dissolved in water and chromatographed by MPLC (CG-161 resin), eluting with a step-wise gradient of methanol in water (0%, 20%, 40%, 60%, 80% and 100%). Three major fractions were collected: 4.07 g eluted with 40% methanol, 2.02 g eluted with 60% methanol and 1.5 g eluted with 80% methanol, respectively. Orange red color spots obtained with Dragendorffs reagent confirmed the presence of alkaloids in these three fractions. The fraction eluted with 40% methanol (190 mg) was further purified by reverse phase preparative HPLC (C18 column; 41.1 mm×250 mm), eluting with a mixture of solvents (water (0.05 M TEA at pH 3.6 with phosphoric acid) and 1% THF in acetonitrile (85:15)) to give 89 mg of a yellow solid, which was further purified on an LH-20 column (2.0 cm×40 cm), eluting with DI water to yield 7.9 mg of a yellow solid, identified as Magnoflorine (see FIG. 1). $(C_{20}H_{24}NO_4)^+$ molecular weight 342.50; mass spectra: ESI+=342, ESI-= 340, FAB=342; UV $\lambda_{max}$ (MeOH) nm: 234, 279, 325; IR γ (KBr): 3400, 2932, 2912, 1598 1515, 1462, 1378; $^1$H NMR (D$_2$O) δ: 2.13 (t,1H), 2.72 (s, 3H), 2.63–3.28 (m, 5H), 3.15 (s, 3H), 3.55 (m,1H), 3.77 (s, 3H), 3.83 (s, 3H) 6.77 (m, 2H), 6.87 (s, 1H); $^{13}$C NMR: 23.24, 29.61, 42.86, 53.62, 55.98, 60.99, 68.63, 110.41, 111.57, 115.56, 119.03, 120.19, 120.47, 121.21, 125.38, 140.33, 140.63 147.99, 149.04.

The fraction eluted with 60% methanol (179 mg) was further purified by reverse phase preparative HPLC (C18 column: 41.1 mm×250 mm), eluting with a mixture of solvents (water (0.05 M TEA at pH 3.6 with phosphoric acid) and 1% THF in acetonitrile (90:10)) to yield 42.9 mg of a solid, which was further purified on an LH-20 column, eluting with water to yield a yellow solid (6.8 mg), which was identified as Laurifoline (see FIG. 1). LC-MS: a single peak at m/z 342, having a different retention time than Magnoflorine; $(C_{20}H_{24}NO_4)^+$ molecular weight 342.41; mass spectra ESI+ m/z=342; UV $\lambda_{max}$ (EtOH) nm: 230, 282, 306; IR γ (KBr): 3400, 2932, 2912, 1598, 1515, 1462, 1378, 1249, 1044; $^1$H NMR (D$_2$O) δ: 1.83 (t,1H), 2.66 (s, 3H), 2.58–3.50 (m, 5H), 3.10 (s, 3H), 3.67 (s, 3H), 3.72 (s, 3H) 6.46 (s,1H), 6.53 (s, 1H), 7.52 (s, 1H); $^{13}$C NMR: 23.96, 2840, 43.44, 54.08, 56.49, 56.61, 62.04, 69.45, 109.78, 112.58, 115.52, 118.88, 119.55, 120.37, 123.64, 125.92, 141.90, 144.99, 146.59, 148.65.

Example 2

Determination of Alkaloid Content in Different Species of Prickly Ash Using Different Methods of Extraction Southern Prickly Ash bark powder (Z. clava-herculis, 100 g ) was extracted exhaustively with hot methanol (Soxhlet extraction) for 48 hours. The methanol extract was evaporated at 40° C. using a rotary evaporator at low pressure to yield a brown sticky solid (24.47 g). The solid was analyzed for alkaloid content and the results are set forth in Table 1. The alkaloid content in the extract was determined to be 9.1% and the total alkaloid content in the bark was determined to be 2.23%.

Prickly Ash bark from three different species of Zanthoxylum (Z. americanum, Z. frazineum and Z. clava-herculis) was ground to a powder using a mechanical grinder. The three samples (60 g, 60 g, and 35 g, respectively) were mixed with 600 mL of distilled water and shaken at room temperature for two hours. The solution was decanted, filtered and the filtrate was freeze dried to give three brown colored powders, which were analyzed for alkaloid content. The results are set forth in Table 1. As can be seen in Table 1, the aqueous extracts contained a high alkaloid content with low extractable solids.

Southern prickly ash bark (Z. clava herculis), three samples, 60 g each, was extracted with 600 mL of three different acidic aqueous solutions (5% tartaric acid, 0.6% sulfuric acid, and 1% HCl, respectively) at 60 ° C. for two hours. The solution was filtered through a Buchner funnel, neutralized with NaOH to pH=7 and the solvent was evaporated with a freeze-drier. Each of the extracts was analyzed for alkaloid content. The results are set forth in Table 1. As can be seen in Table 1, extraction with acidic water solutions increases the amount of extractable solids. The alkaloid concentration in the extracts, however, is decreased.

Dried stem bark from three different Zanthoxylum species (Z. americanum, Z. clava-herculis and Z. frazineum) was ground to a fine powder and extracted with 1% HCL at 60° C. for two hours. The solution was filtered through a Buchner funnel, neutralized with NaOH to pH=7 and the solvent was evaporated with a freeze-drier. The extracts were analyzed for alkaloid content and the results are set forth in Table 1. As can be seen in Table 1, Z. frazineum had a higher total alkaloid content than Z. americanum and Z. clava-herculis. However, the chemical components of Z. frazineum are different from that of Southern and Northern Prickly Ash bark.

Example 3

Commercial Process for the Isolation of Isoquinoline Alkaloids from Prickly Ash Bark Into a 5 L jacketed reactor equipped with a thermocouple connected to a digital thermometer, a condenser and mixer system consisting of a variable speed motor and a 316 SS shaft fitted with an A100 axial flow impeller was placed 2 L of water containing 0.3% v/v of concentrated sulfuric acid. The water was heated to 60° C. with a recirculating bath, after which 350 g of coarsely ground bark (average bulk density 2.9 lb/gal) was added under vigorous stirring. The suspension was vigorously stirred at 60° C. for 54 hours. Aliquots were removed at various time intervals, vacuum filtered while hot over a hydrophilic non-woven polypropylene filter cloth and the crude extract was analyzed for solids and alkaloids. The results after 54 hours of extraction are summarized in Table 2.

The extraction described above was repeated using 3 L of water. Analysis of aliquots removed at various time intervals established that the solid and alkaloid content of the extract leveled off after 24 hours. The solids were removed by vacuum filtration, as described above and crude extract was analyzed for solids and alkaloids. The results are set forth in Table 3.

Ground Prickly Ash bark was next extracted using a column extractor. The column extractor used consisted of a flanged 4" id×59" ht fiberglass column (rated at 80 psi @ 212° F.) equipped with 20-mesh stainless steel frit at the bottom. The bottom outlet of the extractor was equipped with a stainless steel ball valve. The extractor was charged with 2.831 kg of coarsely ground bark (average bulk density of 2.91 lb/gal). The extractor was capped and fitted with a pressure gauge and a stainless steel ball valve, the extractor was connected to a peristaltic pump using PHARMED® LS 24 tubing. Eight liters of room temperature extraction fluid (water containing 0.3% concentrated sulfuric acid) was pumped into the extractor and the mixture was allowed to stand at room temperature for 60 hours. The solvent (first extract) was removed and replaced with 3 L of virgin extraction solvent that was re-circulated with the pump for 6 hours. The two extracts were then analyzed for solids and alkaloids content. The results are shown in Tables 4 and 5.

In a second experiment, the column extractor described above was charged with 2.803 kg of coarsely ground bark (average bulk density of 2.91 lb/gal), and 8 L of extraction fluid (water containing 0.3% concentrated sulfuric acid) at 60° C. was pumped into the extractor and the mixture was allowed to stand at room temperature for 60 hours. The solvent (first extract) was then removed and the bark was extracted a second time with 10 L of the extraction solvent at of 60° C. The fluid was re-circulated for 6 hours at 60° C. using a heat exchanger. The solvent (second extract) was removed and the solids were blown dry with air. The two extracts were analyzed for solids and alkaloid content and the results are set forth in Tables 6 and 7.

The pH of the combined extract was raised to 5 with aqueous sodium carbonate, the resulting material was concentrated 6 fold then freeze-dried to yield 37 g of dried crude extract.

Prickly Ash bark was extracted in a 316 stainless steel column extractor (flanged 10" id×12" ht 316 SS column). The bottom plate was equipped with 20 mesh screen/frit, the outlet was fitted with a teflon coated SS ball valve and the inlet was fitted with a pressure gauge and a teflon coated SS ball valve that was connected to a peristaltic pump using a PHARMED® R LS 24 tubing. The extractor was charged with 4.23 kg of coarsely ground bark (average bulk density of 2.91 lb/gal). After capping the extractor, 12 L of 60° C. extraction fluid (water containing 0.3% v/v concentrated sulfuric acid) was pumped slowly into the reactor, which was allowed to stand overnight at room temperature. The first extract was removed and replaced with 13 L of virgin extraction fluid heated to 60° C. The second extract was re-circulated for 6 hours while maintaining the temperature at 60° C. After the second extract was removed, 5 L of fresh hot solvent was added and the extractor was allowed to stand overnight at room temperature. The third extract was removed and the marc was discarded. Each extract was analyzed for solids and alkaloids content, the results are shown in Tables 8 and 9. The combined crude extract was treated with aqueous sodium carbonate to bring the pH to 5, then concentrated 7 fold. The concentrate was lyophilized to yield 633 g of dried crude extract.

Example 4

Separation of Isoquinoline Alkaloids from Prickly Ash (Aqueous Extract) Using Ion Exchange Chromatography Ion exchange chromatography is used extensively in the separation of ionic organic and inorganic molecules. The quaternary ammonium alkaloids in the aqueous extract of Prickly Ash are ionic compounds, therefore the use of ion exchange chromatography is a useful means to separate the ammonium alkaloids from the crude extract. Analytical grade macroporous cation resin (AG-MP-50, 25–50 mesh hydrogen form) was packed in medium pressure liquid chromatography column (MPLC, I.D. 5.0 cm, 19.6 mL/cm). The column bed was washed with 2N HCl (20 column volumes), 1N NaOH (10 column volumes) and 1N HCl (10 column volumes). The column was then washed with distilled water until the pH of the medium was neutral. A sample of Prickly Ash, aqueous extract (20 g) was mixed with water, decanted and loaded onto the column. The column was washed with water until all of the unbound components were removed. The column was then eluted with ammonium hydroxide (4 column volumes). The ammonium hydroxide eluent was collected and evaporated to yield 1.96 g total alkaloids.

Example 5

Reduction of the Swelling of the Recto-Anus in Croton Oil-Induced Hemorrhoid Model in Rats by Prickly Ash Extract Male SD rats (6 weeks old, approximately 140 g) were purchased from Harlan Sprague Dawley and allowed to acclimate for 1 week. The rats were maintained in a pathogen-free facility in accordance with the National Research Council of Laboratory Animal care and use guidelines. Each experiment was preformed with age-matched rats 7–8 weeks old. The croton oil-induced hemorrhoid model in rats was performed according to the method published by Nishiki (Nishiki el al. (1988) Folia Pharmacology Japan 92:215–225; Nishiki et al. (1988) Folia Pharmacol. Japan 92:227–240). Briefly, a cotton swab with a diameter of 4 mm soaked with 0.16 mL of inducer (deionized water: pyridine: ethyl ether: 6% croton oil/ethyl ether (1:4:5:10) was applied to the rat's anus for 12 seconds. The final concentration of croton oil was 3%. The edema developed linearly until 7–8 hours after application and the severity of the edema was sustained for more than 24 hours. Twenty-four hours later, recto-anus tissue (approx. 10 mm long) was isolated after the rats were euthanized. The weights of rat body and recto-anus were measured. The recto-anus coefficient (RAC) was calculated using the formula: weight of recto-anus (mg)/body weight (g).

The average RAC of croton oil-treated rats was 2.10, which was 38.2% higher than that the rats treated with vehicle only (RAC=1.52). Vehicle alone did cause significant swelling of the recto-anus as compared with the rats without any treatment (RAC=0.98). Twenty-four hours after hemorrhoid induction with croton oil followed by treatment orally with prickly ash extract at either 6 mg/kg or 30 mg/kg and by treatment topically with prickly ash extract at 6 mg/mL in 1:1 aquaphor, the RAC of rats was determined. The results are depicted in FIG. 2, which shows that the prickly ash extract completely inhibited the swelling of the recto-anus induced by croton oil at both concentrations and by both routes of administration.

Example 6

Reduction of the Swelling of the Recto-Anus in Croton Oil-Induced Hemorrhoid Model in Rats by Alkaloids Isolated from Prickly Ash This experiment was performed as described in Example 5. The average RAC of croton oil-treated rats was 1.92, which was 20% higher than that the rats treated with vehicle only (RAC=1.60) in this experiment. Vehicle alone did cause significant swelling of the recto-anus as compared with the rats without any treatment (RAC=0.98). Twenty-four hours after hemorrhoid induction with croton oil followed by treatment orally with the pure alkaloids isolated from prickly ash extract at 1 mg/kg, the RAC of rats was determined. As shown in FIG. 3, Magnoflorine completely inhibited the swelling of the recto-anus induced by croton oil. Under the same conditions, Laurifoline and Chelerythrine partially reduced the swelling.

Example 7

Dose Dependent Reduction of the Swelling of the Recto-Anus in Croton Oil-Induced Hemorrhoid Model in Rats by Prickly Ash Extract This experiment was performed as described in Example 5. The average RAC of croton oil-treated rats was 1.66 which was 40.7% higher than that of the rats treated with vehicle only (RAC=1.18). Twenty-four hours after hemorrhoid induction with croton oil, followed by oral treatment with Prickly Ash extract at doses of 6.0 mg/kg, 2.0 mg/kg, and 0.67 mg/kg, the RAC of rats was determined. As shown in FIG. 4, the Prickly Ash extract reduced the swelling of the recto-anus by 79.5%, 67.5% and 42.1%, respectively.

TABLE 1

Alkaloid Content in Various Zanthoxylum Species

| Latin Name | Plant part | Sample Weight | Solvent | Total Solids (g) | Extractable Solids | Alkaloid content |
|---|---|---|---|---|---|---|
| Zanthoxylum clava-herculis | Stem bark | 100 g | MeOH (reflux) | 24.47 | 24.47% | 9.1% |
| Zanthoxylum americanum | Stem bark | 60 g | $H_2O$ | 2.65 | 4.4% | 35.3% |
| Zanthoxylum frazineum | Stem bark | 60 g | $H_2O$ | 6.6 | 11% | 22.4% |
| Zanthoxylum clava-herculis | Stem bark | 35 g | $H_2O$ | 3.58 | 10.2% | 25.4% |
| Zanthoxylum clava-herculis | Stem bark | 60 g | $H_2O$ (5% tartaric acid) | 8.6 | 14.3% | 2.0% |
| Zanthoxylum clava-herculis | Stem bark | 60 g | $H_2O$ (0.6% $H_2SO_4$) | 7.56 | 12.6% | 6.5% |
| Zanthoxylum clava-herculis | Stem bark | 60 g | MeOH (1% HCl) | 16.51 | 27.5% | 4.7% |
| Zanthoxylum americanum | Stem bark | 60 g | MeOH (1% HCl) | 13.69 | 22.8% | 2.2% |
| Zanthoxylum frazineum | Stem bark | 60 g | MeOH (1% HCl) | 18.57 | 31% | 9.9% |

TABLE 2

Extraction of Prickly Ash Solids with 0.3% $H_2SO_4$ in 2 L $H_2O$

| Parameter | Value | Yield |
|---|---|---|
| Liquid Extract | 750 mL | 37.5% |
| Solids | 28.44 g | 8.13% |
| Alkaloids | 0.96 g | 0.27% |
| Purity of Alkaloids | | 3.27% |

TABLE 3

Extraction of Prickly Ash Solids with 0.3% $H_2SO_4$ in 3 L $H_2O$

| Parameter | Value | Yield |
|---|---|---|
| Liquid Extract | 1900 mL | 63.3% |
| Solids | 52.82 g | 16.1% |
| Alkaloids | 3.82 g | 1.16% |
| Purity of Alkaloids | | 7.23% |

TABLE 4

Extraction of Solids with Column Extractor - Room Temperature

| | First Extract | | Second Extract | |
|---|---|---|---|---|
| | Value | Yield | Value | Yield |
| Liquid Extract | 2.75 L | 34.4% | 2.9 L | 93.6% |
| Solids | 114.3 g | 4.0% | 87.3 g | 3.1% |
| Alkaloids | 13.1 g | 0.46% | 10.6 g | 0.37% |
| Purity of Alkaloids | 11.5% | | 12.1% | |

TABLE 5

Combined Results from Table 4

| Parameter | Value | Yield |
|---|---|---|
| Liquid Extract | 5.65 L | 50.1% |
| Solids | 201.6 g | 7.1% |
| Alkaloids | 23.7 g | 0.82% |
| Purity of Alkaloids | | 11.7% |

TABLE 6

Extraction of Solids with Column Extractor at 60° C.

| | First Extract | | Second Extract | |
|---|---|---|---|---|
| | Value | Yield | Value | Yield |
| Liquid Extract | 2.7 L | 33.75% | 9.5 L | 95.0% |
| Solids | 135.3 g | 4.8% | 199.8 g | 7.13% |
| Alkaloids | 16.2 g | 0.58% | 29.35 g | 1.05% |
| Purity of Alkaloids | 11.97% | | 14.7% | |

TABLE 7

Combined Results from Table 6

| Parameter | Value | Yield |
|---|---|---|
| Liquid Extract | 12.2 L | 67.8% |
| Solids | 335.1 g | 11.96% |
| Alkaloids | 45.55 g | 1.63% |
| Purity of Alkaloids | | 13.59% |

TABLE 8

Extraction with Column Extractor at 60° C.

| | First Extract | | Second Extract | | Third Extract | |
|---|---|---|---|---|---|---|
| | Value | Yield | Value | Yield | Value | Yield |
| Liquid Extract | 5.0 L | 41.67% | 11.0 L | 84.62% | 5.0 L | 100.0% |
| Solids | 103.5 g | 2.45% | 409.2 g | 9.67% | 95.5 g | 2.26% |
| Alkaloids | 11.15 g | 0.26% | 34.1 g | 0.81% | 7.65 g | 0.18% |
| Purity of Alkaloids | 10.8% | | 8.33% | | 8.01% | |

TABLE 9

Combined Results from Table 8

| Parameter | Value | Yield |
|---|---|---|
| Liquid Extract | 21.0 L | 70% |
| Solids | 608.2 g | 14.38% |
| Alkaloids | 52.9 g | 1.25% |
| Purity of Alkaloids | | 8.70% |

What is claimed is:

1. A method of treating varicose veins and hemorrhoids comprised of the administration to a patient in need thereof an effective amount of a composition consisting essentially of an isoquinoline alkaloid and a pharmaceutically acceptable carrier.

2. The method of claim 1 wherein said isoquinoline alkaloid is obtained by organic synthesis.

3. The method of claim 1 wherein said isoquinoline is isolated from a plant.

4. The method of claim 3 wherein said plant is selected from the group consisting of the following genera: Zanthoxylum, Tinospora, Mahonia, Phellodendron, Aristolochia, Magnolia, Thalictrum, Coptis, Epimedium, Ranunculus, Sinomenium, Nandina, Manodora, Berberis, Fumaria, Chelidonium, Pachygone, Dioscoreophyllum, Glaucium, Clematis, Aconitum or Cocculus, Xanthoxylium, Toddalia, Papaver, Hypecoum, Hylomecon, Prantl, Argemone, Eschscholtxia, Sanguinaria, Corydalis, Dicentra, Fagara, Symphoricarpos, Bocconia, Xylocarpus, and Mocleaya.

5. The method of claim 3 wherein the isoquinoline alkaloid is obtained from the stem and root bark or whole plant.

6. The method of claim 1 wherein the composition is pharmaceutically formulated for enteral administration, parenteral administration and topical application at a dose selected from 0.01 to 50 mg/kg of body weight.

7. A method of treating varicose veins and hemorrhoids comprised of the administration to a patient in need thereof an effective amount of a composition consisting essentially of an isoquinoline alkaloid, wherein said isoquinoline alkaloid is selected from an aporphine alkaloid or a benzophenanthridine alkaloid and a pharmaceutically acceptable carrier.

8. The method of claim 7 wherein said aporphine alkaloid is selected from the group of compounds having the following structure:

wherein $R_1$ and $R_2$ are independently selected from the group consisting of H, alkyl, substituted alkyl, cycloalkyl, substituted cycloalkyl, alkenyl or substituted alkenyl; $R_3$, $R_4$, $R_5$, $R_6$, $R_7$ and $R_8$ are independently selected from the group consisting of H, hydroxy, thiol, methoxy, methyl sulfide, methylenedioxy, alkoxy, alkyl sulfide; and the pharmaceutically acceptable acid addition salts, selected from the group consisting of chloride, iodide, fluonde, sulfate, phosphate, acetate or carbonate.

9. The method of claim 7 wherein said aporphine alkaloid is selected from Magnoflorine or Laurifoline.

10. The method of claim 7 wherein said benzophenanthridine alkaloid is selected from the group of compounds having the following structure:

wherein $R_1$, $R_2$, $R_3$ and $R_4$ are independently selected from the group consisting of H, hydroxy, alkoxy, methoxy, methylenedioxy, thiol, methyl sulfide and alkyl sulfide; and $R_5$ is selected from the group consisting of H, alkyl, substituted alkyl, cycloalkyl, substituted cycloalkyl, alkenyl and substituted alkenyl; and the pharmaceutically acceptable acid addition salts selected from the group consisting of chloride, iodide, fluoride, sulfate, phosphate, acetate and carbonate.

11. The method of claim 7 wherein said benzophenanthridine alkaloid is Chelerythrine.

* * * * *